United States Patent
Schneider

(10) Patent No.: US 10,156,656 B2
(45) Date of Patent: Dec. 18, 2018

(54) APPARATUS AND METHODS FOR DETERMINING REAL-TIME HOLE CLEANING AND DRILLED CUTTINGS DENSITY QUANTIFICATION USING NUCLEONIC DENSITOMETERS

(71) Applicant: Christopher D. Schneider, Richmond, TX (US)

(72) Inventor: Christopher D. Schneider, Richmond, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 19 days.

(21) Appl. No.: 14/935,208

(22) Filed: Nov. 6, 2015

(65) Prior Publication Data

US 2017/0131429 A1   May 11, 2017

(51) Int. Cl.
| | | |
|---|---|---|
| *G01V 5/10* | (2006.01) | |
| *G01N 9/24* | (2006.01) | |
| *E21B 21/00* | (2006.01) | |
| *E21B 21/06* | (2006.01) | |
| *E21B 21/08* | (2006.01) | |

(Continued)

(52) U.S. Cl.
CPC .............. *G01V 5/101* (2013.01); *E21B 21/00* (2013.01); *E21B 21/01* (2013.01); *E21B 21/065* (2013.01); *E21B 21/08* (2013.01); *E21B 49/005* (2013.01); *G01N 9/24* (2013.01); *G01N 23/00* (2013.01); *G01V 5/08* (2013.01); *E21B 44/005* (2013.01); *E21B 49/00* (2013.01)

(58) Field of Classification Search
CPC .................................................... G01V 5/101
See application file for complete search history.

(56) References Cited

U.S. PATENT DOCUMENTS 4,485,675 A * 12/1984 Verret ...................... G01N 9/28
                                                                73/439
5,012,091 A *  4/1991 Moake ..................... G01V 5/12
                                                               250/262

(Continued)

FOREIGN PATENT DOCUMENTS

WO      2014037731 A1      3/2014

OTHER PUBLICATIONS

Tracerco, "Density Gauge Measurement in the Process Industry", publicly available on Oct. 15, 2011 at http://www.tracerco.com/instrumentation/density-measurement—see Wayback Machine report, accessed on Apr. 18, 2017, pp. 1-4.*

(Continued)

*Primary Examiner* — David Porta
*Assistant Examiner* — Jeremy S Valentiner
(74) *Attorney, Agent, or Firm* — Cantor Colburn LLP

(57) ABSTRACT

An apparatus for determining density of fluid returning from a wellbore ("return fluid") during drilling of the wellbore being drilled using a drill string having a drill bit at an end thereof is disclosed. The apparatus in one embodiment includes a first nucleonic densitometer placed on outside of a return line carrying the return fluid from the wellbore that includes drilling fluid supplied to the drill string and cuttings cut by the drill bit during drilling of the wellbore and a processor that determines the density the return fluid from measurements provided by first nucleonic densitometer.

18 Claims, 1 Drawing Sheet

(51) Int. Cl.
*G01V 5/08* (2006.01)
*G01N 23/00* (2006.01)
*E21B 21/01* (2006.01)
*E21B 44/00* (2006.01)
*E21B 49/00* (2006.01)

(56) References Cited

U.S. PATENT DOCUMENTS

| | | | |
|---|---|---|---|
| 6,357,536 | B1 | 3/2002 | Schrader et al. |
| 6,637,524 | B2 | 10/2003 | Kruspe et al. |
| 7,657,392 | B2 | 2/2010 | Gysling |
| 8,130,591 | B2 | 3/2012 | Geerits |
| 8,583,377 | B2 | 11/2013 | Moake |
| 8,636,060 | B2 | 1/2014 | Hernandez |
| 8,775,089 | B2 | 7/2014 | Van Zuilekom et al. |
| 8,818,779 | B2 | 8/2014 | Sadlier et al. |
| 8,965,703 | B2 | 2/2015 | Prakash et al. |
| 2009/0194330 | A1* | 8/2009 | Gray ............ E21B 21/00 175/24 |
| 2009/0196120 | A1* | 8/2009 | Geerits ............ G01V 1/50 367/35 |
| 2009/0260430 | A1* | 10/2009 | Zamfes ............ E21B 21/08 73/152.04 |
| 2011/0174541 | A1 | 7/2011 | Strachan et al. |
| 2013/0090854 | A1* | 4/2013 | Rasmus ............ G01V 9/00 702/9 |
| 2013/0110404 | A1* | 5/2013 | Moake ............ E21B 47/1015 702/8 |
| 2013/0119245 | A1* | 5/2013 | DiFoggio ............ G01N 9/24 250/252.1 |
| 2013/0168100 | A1* | 7/2013 | Judge ............ E21B 21/08 166/336 |
| 2014/0190747 | A1 | 7/2014 | Hay |
| 2014/0291023 | A1 | 10/2014 | Edbury et al. |
| 2014/0336936 | A1 | 11/2014 | Inanc |
| 2015/0212045 | A1* | 7/2015 | Raykhman ............ G01N 29/4472 73/32 A |

OTHER PUBLICATIONS

Fredagsvik, K. ; University of Stavanger, Faculty of Science and Technology, Master's Thesis; 2014, pp. 1-101.

PCT International Search Report and Written Opinion; International Application No. PCT/US2016/059903; International Filing Date: Nov. 1, 2016; dated Feb. 13, 2017; pp. 1-13.

* cited by examiner

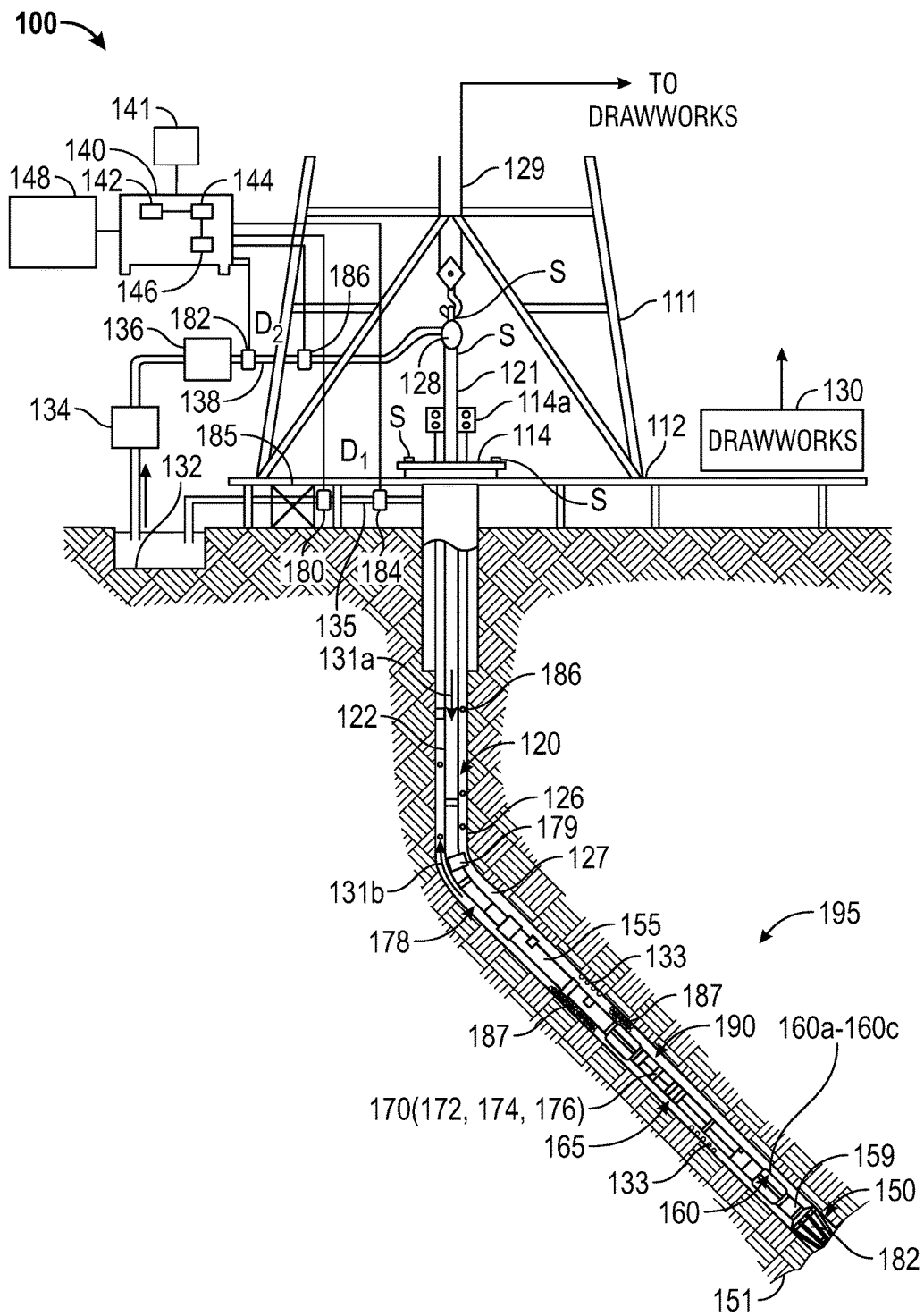

APPARATUS AND METHODS FOR DETERMINING REAL-TIME HOLE CLEANING AND DRILLED CUTTINGS DENSITY QUANTIFICATION USING NUCLEONIC DENSITOMETERS

BACKGROUND

1. Field of the Disclosure

This disclosure relates generally to apparatus and methods for determination of real-time hole cleaning and quantification of drilled cuttings during drilling of wellbores.

2. Background of the Art

Wellbores (also referred to herein as "wells" or "boreholes") are drilled in subsurface formations for the production of hydrocarbons (oil and gas) trapped in zones at different depths. A large number of wells drilled exceed 15,000 feet and include relatively long deviated and horizontal sections. Such wells are drilled using a drill string that includes a drilling assembly (commonly referred to as the "bottomhole assembly" or "BHA") at the bottom end of a drill pipe. The BHA includes a variety of sensors and devices and a drill bit attached at the bottom end of BHA. The drill string is conveyed into the well. To drill the well, the drill bit is rotated by rotating the drill string from the surface and/or by a mud motor placed in the BHA. A drilling fluid (commonly referred to as "mud") is supplied under pressure from the surface into the drill pipe, which fluid discharges at the bottom of the drill bit and returns to the surface via the spacing between the drill string and the well (referred to as the "annulus"). The returning fluid (also referred to herein as the "return fluid") contains the rock bits disintegrated by the drill bit, commonly referred to as the cuttings. The return fluid also sometimes contain gas and/or oil and/or water due to the influx from the formation. The return fluid, thus, often is a multiphase fluid with entrained solids. In horizontal and highly deviated wells, the cuttings sometime accumulate at the low side of such wells due to lack of adequate flow rate of the supplied drilling fluid and/or high density of the cuttings. At other times, the drilling fluid may enter the formation, in part, due to excessive overburden due to the weight of the fluid column in the wellbore or a relatively soft formation. At other times, the rock from the formation surrounding the wellbore may cave into the wellbore due to presence of a soft formation and/or high drilling fluid flow rate. When all the cuttings are removed as produced, the hole is said to be cleaning efficiently or effectively. Operators take remedial actions to alleviate the above-noted adverse conditions, once determined. The parameters controlled by the operator include the density of the fluid supplied to the wellbore and the flow rate of the supplied fluid. The density of the supplied fluid is controlled within a desired range to maintain a desired overburden The present methods for measuring wellbore stability and influx from the formation commonly utilize Coriolis flow meters installed in the return line. These instruments are accurate when installed in a pipe that is completely full. However, the Coriolis flow meters are not always acceptably accurate when multi-phase fluid is present, such as fluid containing gas or when an air gap is present in the flow line. The air gap in the flow line sometimes is addressed by physically modifying the geometry of the return flow line that prevents the forming of the air gap.

The present methods for determining density of the return fluid for determining wellbore stability and hole cleaning efficiency utilizes a mass balance or scale that is affixed to the end of shale shakers installed to remove the solids from the return fluid. The shale shakers separate from the cuttings from the return fluid. The cuttings are passed to the mass balance to weigh the cuttings. The measured weight and/or volume of the cuttings is compared against the theoretical quantity of "dry" cuttings, as the weighted cuttings still include some amount of fluid. This method thus utilizes a correction factor that assumes the quantity of drilling fluid remaining in the cuttings when they are weighed.

It is important during drilling to maintain the drilling fluid density and thus equivalent circulating density (ECD) between the formation pore pressure and formation fracture gradient to avoid blow outs and fracturing of the formation. Too low ECD will likely yield an influx and possibly wellbore instability issues related to caving. Too high ECD will likely lead to fracturing of the formation and potentially loss of drilling fluid into the formation. The present methods for determining the desired drilling fluid density range involves calculations based on assumptions of formation depositions and original fluid type, i.e., saltwater in marine basins and their corresponding pressure gradients. These pore pressure models are adjusted with physical measurements, such as shale density. Shale density at depth is used to calculate an overburden gradient (OBG). Subsequently, Fracture Gradient and Pore Pressure Gradients are calculated using OBG determined from physical measurements instead of models. This results in more representative and accurate pore pressure calculations and increased insight and understanding into formation properties, leading to more successful drilling operations. These methods, however are not based on real time determination of density of the cuttings correlated to the wellbore depth. Thus, there is a need to determine in real time the density of the return fluid and the amount of cuttings in the return fluid that can be utilized to further determine other parameters, including desired drilling fluid density, pressure gradient, hole cleaning efficiency, gas/oil/water influx, caving, fracturing, and pore pressure.

The disclosure herein provides apparatus and methods for real time determination of density of the return fluid and the amount of cuttings in the return fluid from which other desired wellbore parameters may be determined.

SUMMARY

In one aspect, an apparatus for determining density of fluid returning from a wellbore ("return fluid") during drilling of the wellbore using a drill string having a drill bit at an end thereof is disclosed. The apparatus, in one embodiment, includes a nucleonic densitometer placed on outside of a return line carrying the return fluid from the wellbore that includes drilling fluid supplied to the drill string and cuttings cut by the drill bit during drilling of the wellbore, and a processor that determines the density the return fluid and the amount of cuttings in the return fluid from the measurements provided by nucleonic densitometer.

In another, a method of determining density of a fluid returning from a wellbore during drilling of the wellbore using a drill string having a drill bit at an end thereof. The method includes: providing a nucleonic densitometer placed on or attached to an outside of a return line carrying the return fluid from the wellbore that includes drilling fluid supplied to the drill string and cuttings cut by the drill bit during drilling of the wellbore; and determining in real time, using a processor, the density of the return fluid and the amount of cuttings in the return fluid from measurements provided by nucleonic densitometer.

Examples of the more important features of completion system have been summarized rather broadly in order that the detailed description thereof that follows may be better understood, and in order that the contributions to the art may be appreciated. There are, of course, additional features that will be described hereinafter and which will form the subject of the claims.

BRIEF DESCRIPTION OF THE DRAWINGS

For a detailed understanding of the apparatus and methods disclosed herein, reference should be made to the accompanying drawings and the detailed description thereof, wherein like elements are generally given same numerals and wherein:

FIG. 1 shows an exemplary drilling system for drilling a wellbore that shows well sections wherein cutting accumulation and caving has occurred along with nucleonic sensors used by a processor for determining certain parameters of interest including, density of fluid supplied to the wellbore, density of the return fluid and percent of cuttings in the return fluid.

DETAILED DESCRIPTION

In general, the disclosure provides a drilling system that utilizes one or more nucleonic densitometers clamped onto the exterior of the flow line supplying drilling fluid to the drill string and to the return flow line to determine in real time various parameters relating to the drilling of the wellbore, including, drilling fluid density, return fluid density, flow rate, and cuttings/solids amount (volume and/or percent of solids in the return fluid). The system and methods further determine from the same sensors the flow rate of the fluid supplied into the wellbore and flow rate of the return fluid. Additionally, the system and methods provided herein determine in real time the equivalent circulating density, cuttings accumulation in the wellbore, caving of formation into the wellbore and influx of gas/oil/water from the formation into the wellbore. Furthermore, once lithology of cuttings over depth drilled is determined either from physical samples or electric logs from the sensors in the drilling assembly, this disclosed system may be used to determine shale density values. The determined shale density values may then be used to determine overburden gradient (OBG). Formation pore pressure and fracture pressure may then be determined using the OBG. This allows for pore pressure calculations to be performed using direct real time density measurements instead of using estimates from modeling, thereby increasing accuracy of formation pore pressure and fracture pressure values when measurement-while-drilling density tools are not utilized.

FIG. 1 is a schematic diagram of an exemplary drilling system 100 that includes a drill string 120 having a drilling assembly (also known as a bottomhole assembly or "BHA" 190 attached to its bottom end. Drill string 120 is shown conveyed in a wellbore (also referred herein as well or borehole) 126 being formed in a formation 195. The drilling system 100 includes a conventional derrick 111 erected on a platform or floor 112 that supports a rotary table 114 that is rotated by a prime mover, such as an electric motor (not shown), at a desired rotational speed. A tubing or drill pipe (such as made by joining pipe sections) 122, having the drilling assembly 190 attached at its bottom end, extends from the surface to the bottom 151 of the borehole 126. A drill bit 150, attached to the bottom of the drilling assembly 190, disintegrates the geological formation 195 when the drill bit 150 is rotated by rotating the drill string 120 from the surface and/or by a mud motor 155 in the BHA 190. The drill string 120 is coupled to a draw works 130 via a Kelly joint 121, swivel 128 and line 129 through a pulley. Draw works 130 is operated to control the weight on bit ("WOB"). The drill string 120 may be rotated by a top drive 114a rather than the prime mover and the rotary table 114.

The drilling assembly 190 may also contain formation evaluation sensors or devices (also referred to as measurement-while-drilling (MWD) or logging-while-drilling (LWD) sensors) for providing various properties of interest of the formation 195, including, but not limited to, resistivity, density, porosity, permeability, acoustic properties, nuclear-magnetic resonance properties, corrosive properties of the fluids or the formation, salt or saline content, and other selected properties of the formation 195. Such sensors are generally known in the art and for convenience are collectively denoted herein by numeral 165. The drilling assembly 190 may further include a variety of other sensors and communication devices 159 for controlling and/or determining one or more functions and properties of the drilling assembly 190 (including, but not limited to, velocity, vibration, bending moment, acceleration, oscillation, whirl, and stick-slip) and drilling operating parameters, including, but not limited to, weight-on-bit, fluid flow rate, and rotational speed of the drilling assembly.

Still referring to FIG. 1, the drill string 120 further includes a power generation device 178 configured to provide electrical power or energy to sensors 165, devices 159 and other devices. Power generation device 178 may be located in the drilling assembly 190 or drill string 120. The drilling assembly 190 further includes a steering device 160 that includes steering members (also referred to a force application members) 160a, 160b, 160c that may be configured to independently apply force on the borehole 126 to steer the drill bit along any desired direction. A downhole control unit 170 processes data from downhole sensors and controls operation of various downhole devices. The control unit includes a processor 172, such as microprocessor, a data storage device 174, such as a solid-state memory and programs 176 stored in the data storage device 174 and accessible to the processor 172. A suitable telemetry unit 179 provides two-way signal and data communication between a surface control unit 140 and downhole control unit 170.

To drill the wellbore 126, a suitable drilling fluid 131a (also referred to as the "mud") from a source thereof, such as a mud pit 132, is supplied under pressure into the drill string 120 by a mud pump 134. The drilling fluid 131a passes from the mud pump 134 into the drill string 120 via a desurger 136 and the fluid line 138 (also referred herein as the inflow fluid line). The drilling fluid 131a discharges at the borehole bottom 151 through openings in the drill bit 150. The fluid 131a discharged at the bottom carries the cuttings (rock disintegrated by the drill bit) returns to the surface through the annular space or annulus 127 between the drill string 120 and the wellbore 126 via a return line 135 (also referred herein as out flow line). The return fluid 131b returning to the surface carries cuttings 133 therewith. The return fluid 131b is a mixture (also referred herein as "slurry") of the fluid 131a supplied to the drill string 120 and the cuttings 133. The return fluid is passed through a separator 185 that removes the cuttings from the returning drilling fluid 131b. The clean fluid is discharged into the mud pit 132 and recirculated. Various sensors "S" provide information about selected parameters, including, but not limited to, drill string torque, rotational speed of the drill string, weight on the drill bit, and rate of penetration of the drill bit.

Still referring to FIG. 1, in one non-limiting embodiment, system 100 includes a nucleonic densitometer 180 strapped on an outside of the return line 135 before the separator 185 for determining in real-time the density of the return fluid 131b. Another nucleonic densitometer 182 may be strapped on the outside of the inflow line 138 for determining in real time the density of the drilling fluid 131a supplied to the drill string 120. Another nucleonic densitometer 184 may be strapped on the outside of the return line 135 a selected distance $D_1$ from the nucleonic densitometer 180 for determining in real time the flow rate of the return fluid 131b. Similarly, another nucleonic densitometer 186 may be paced on the outside of the inflow line 138 a selected distance $D_2$ from the nucleonic densitometer 182 for determining in real time the flow rate of the fluid 131a supplied to the drill string 120. The density and flow rate measurements are then utilized to determine in real time various parameters during drill of the wellbore 126 as described in more detail later. This system determines the densities of the supplied and return fluid without the sensor contacting the fluid flowing through the pipes. A nucleonic densitometer includes a radioactive source that induces radioisotopes into the fluid moving through the pipe on one side of the pipe. A scintillator, such as a sodium iodide crystal, on the opposite side of the pipe receives the gamma rays from the fluid. A photomultiplier tube attached to the scintillator produces photons corresponding to the received gamma rays. Electronic circuits associated with nucleonic densitometer provide count rate from which the density of the fluid flowing through the pipe may be determined. Nucleonic densitometers are known and are thus not described in more detail herein. Also, algorithms and computer programs are available that may be used to determine density from the nucleonic densitometers.

Still referring to FIG. 1, a surface control unit 140 is provided for determining in real time various parameters of interest from the measurements provided by the nucleonic densitometers 180, 182, 184 and 186. The surface control unit 140 may also be used to determine various parameters from sensors S and information provided by various other sensors and devices in the BHA via the telemetry 179. The surface control unit 140 may be a computer-based system that includes a processor 142 (such as a microprocessor), a storage device 144, such as a solid-state memory, tape or hard disc, and one or more computer programs 146 stored in the storage device 144 that are accessible to the processor 142 for executing instructions contained in such programs. The surface control unit 140 displays information about various determined parameters on display 141 for the operator and may further communicate with a remote control unit 148. The surface control unit 140 may further control one or more drilling operations.

Still referring to FIG. 1, prior to drilling the wellbore 126, operators determine the density of the drilling fluid to be supplied to the drill string 120 based on the well profile and knowledge of the formations through which the well will be drilled to maintain the desired pressure gradient in the wellbore, i.e., desired overburden throughout the well depth. The operators also determine the flow rate of the drilling fluid 131a needed for efficient hole cleaning. Once the well is drilled, actual formations may differ from the anticipated formations. In the system 100, during drilling of the wellbore 126, the nucleonic densitometer 182 on the inflow fluid line 138 provides measurements relating to the density of the supplied drilling fluid 131a and the nucleonic densitometer 180 provides measurements relating to the density of the return fluid 131b. The processor 142 at the surface determines in real-time the density of the fluid 131a being supplied to the drill sting 120 from the measurements of the nucleonic densitometer 182 and the density of the return fluid 131b from the measurements from the nucleonic densitometer 180. The processor 142 further determines, in real time, the amount of cuttings 133, such as percent of solids, in the return fluid 131b from the density of the return fluid 131b and the density of the fluid 131a supplied to the drill sting 120. The processor 142 correlates the density of the return fluid to the wellbore depth based on the flow rate and the travel time of the fluid. In addition, the processor 142 determines the flow rate of the fluid 131a being supplied to the drill string 120 from the nucleonic densitometers 182 and 186 and the flow rate of the return fluid 131b from the nucleonic densitometers 180 and 184. Computer algorithms and programs are available that may be used to determine the density and flow rates and are thus not described in detail herein. The processor 142 then correlates in real time the flow rates to the determined densities to correlate the density to the wellbore depth. Using the density and depth measurements, the processor 142 provides in real time the pressure gradient of the fluid column in the wellbore 126 and thus the ECD. This allows the operator to manage the ECD based on actual real time density measurements.

Still referring to FIG. 1, if the density of the return fluid 131b is less than the expected density, it may imply accumulation of rock in the wellbore 126 at the correlated depth. The processor 142 may also determine the extent of the rock accumulation from the difference between the determined density and expected density of the return fluid. The cuttings 133 tends to accumulate on the low side of a deviated or horizontal wells if the density of the rock is high and/or the flow rate of the supplied fluid is not sufficient to move all of the rock being cut through the annulus 127. An example of rock accumulation on low side of the deviated section of the wellbore 126 is denoted by 187. The operator, based on the rock accumulation information, may increase the flow rate of the supplied fluid 131a and/or increase the density of the supplied fluid 131a and/or introduce additives into the supplied fluid 131a to aid in moving the accumulated rock and the rock being cut. The operator may take other remedial actions, such as stopping or slowing down the drilling, but continuing to circulate the drilling fluid 131a through the wellbore 126 to move the accumulated cuttings and clean the hole to a satisfactory level. The rock accumulation may be displayed on display 141 as a function of depth for visual realization by the operator. Based on the accumulated quantity of the rock at a certain depth, the processor may provide a solution, including calculating the desired flow rate and/or density of the supplied fluid 131a.

Still referring to FIG. 1, it is known that gas (methane), oil and salt water are typically present in producing zones and that the density of gas is less than the density of oil, which is less than that of salt water. The processor 142 may be programmed to determine from the density of the return fluid 131b when gas, oil or salt water is present in the return fluid 131b and the corresponding wellbore depth, Thus, when the density of the return fluid is less than the density of the supplied fluid, the processor 142 may provide the amount and location of the influx of gas/oil/water in real time during drilling of the wellbore. However, if the density of the return fluid is greater than the expected density, it indicates caving. The processor 142 may be programmed to determine the extent and corresponding wellbore depth of caving from the determined density and the flow rate. In addition, once lithology of cuttings over wellbore depth is determined either from physical samples or electric logs, the processor 142 may be programmed to determine shale density. Such programs are available and thus not described in detail herein. The determined shale density values may then be used in overburden gradient (OBG). Formation pore pressure and fracture pressure may then be determined using the OBG established from the measurements. This allows for pore pressure calculations to be performed using direct density measurements instead of using estimates from modeling, thereby increasing accuracy of formation pore pressure and fracture pressure values when measurement-while-drilling density tools are not utilized.

The foregoing disclosure is directed to the certain exemplary non-limiting embodiments. Various modifications will be apparent to those skilled in the art. It is intended that all such modifications within the scope of the appended claims be embraced by the foregoing disclosure. The words "comprising" and "comprises" as used in the claims are to be interpreted to mean "including but not limited to". Also, the abstract is not to be used to limit the scope of the claims.

The invention claimed is:

1. An apparatus for determining density of a fluid from a wellbore, comprising:
   a first and second nucleonic densitometer separated by a first distance on an outside surface of an inflow line providing a fluid to a drill string for obtaining density measurements of the fluid in the inflow line;
   a third and fourth nucleonic densitometer separated by a second distance on an outside surface of a return line having the return fluid within for obtaining density measurements of the fluid in the return line, wherein the return fluid includes drilling fluid and cuttings; and
   a processor configured to:
      obtain measurements of density of the fluid in the inflow line at the first nucleonic densitometer and the second nucleonic densitometer,
      determine a flow rate of the fluid in the inflow from the density measurement at the first nucleonic densitometer, the density measurement at the second nucleonic densitometer and the first distance,
      obtain measurements of density of the fluid in the return line at the third nucleonic densitometer and the fourth nucleonic densitometers,
      determine a flow rate of the fluid in the return line from the density measurement at the third nucleonic densitometer, the density measurement at the fourth nucleonic densitometer and the second distance, and
      determine, from the density of the fluid in the inflow line and the density of the fluid in the return line, an amount of cuttings in the return fluid;
      correlate the amount of cuttings in the return fluid to a wellbore depth using the flow rate of the fluid in the return line to determine an accumulation of rock in the wellbore; and
      determine a flow rate of fluid in the inflow line for removing the accumulated rock from the wellbore.

2. The apparatus of claim 1, wherein the processor determines percent of solids in the return fluid using one of: determined density of the return fluid and determined density of the fluid supplied to the drill string; and determined density of the return fluid and a predetermined density of the fluid supplied to the drill string.

3. The apparatus of claim 2, wherein the processor determines from one of the density and percent of solids in the return fluid a wellbore condition that is selected from a group consisting of: accumulation of rocks in the wellbore; caving of a formation into the wellbore; influx of gas into the wellbore; influx of oil into the wellbore; and influx of water into the wellbore.

4. The apparatus of claim 3, wherein the processor correlates the determined condition of the wellbore to a depth in the wellbore.

5. The apparatus of claim 1, wherein the processor determines from the determined density of the return fluid a pore pressure of formation surrounding the wellbore at a selected wellbore depth.

6. The apparatus of claim 1, wherein the processor provides a pressure gradient of the wellbore during drilling of the wellbore.

7. The apparatus of claim 1, wherein the processor determines a desired density of the drilling fluid to be supplied to the drill string to maintain the wellbore overbalanced.

8. The apparatus of claim 1, wherein the processor determines effectiveness of hole cleaning during drilling of the wellbore from the determined density of the return fluid.

9. A method of determining density of a fluid from a wellbore, the method comprising:
   placing a first and second nucleonic densitometer separated by a first distance on an outside surface of an inflow line providing the fluid to the wellbore;
   placing a third and fourth nucleonic densitometer separated by a second distance on an outside surface of a return line carrying the fluid from the wellbore, wherein the fluid in the return line includes cuttings from the wellbore; and
   using a processor to:
      obtain measurements of density of the fluid in the inflow line at the first nucleonic densitometer and the second nucleonic densitometer,
      determine a flow rate of the fluid in the inflow from the density measurement at the first nucleonic densitometer, the density measurement at the second nucleonic densitometer and the first distance,
      obtain measurements of density of the fluid in the return line at the third nucleonic densitometer and the fourth nucleonic densitometer,
      determine a flow rate of the fluid in the return line from the density measurement at the third nucleonic densitometer, the density measurement at the fourth nucleonic densitometer and the second distance, and
      determine, from the density of the fluid in the inflow line and the density of the fluid in the return line, an amount of cuttings in the return fluid;
      correlate the amount of cuttings in the return fluid to a wellbore depth using the flow rate of the fluid in the return line to determine an accumulation of rock in the wellbore; and
      determine a flow rate of fluid in the inflow line for removing the accumulated rock from the wellbore.

10. The method of claim 9 further determining by the processor percent of solids in the return fluid using one of: determined density of the return fluid and determined density of the fluid supplied to the drill string; and determined density of the return fluid and a predetermined density of the fluid supplied to the drill string.

11. The method of claim 10 further comprising determining from one of the density and percent of solids in the return fluid a wellbore condition that is selected from a group consisting of: accumulation of rocks in the wellbore; caving of a formation into the wellbore; influx of gas into the wellbore; influx of oil into the wellbore; and influx of water into the wellbore.

12. The method of claim 11 further comprising correlating, using the processor, the determined condition of the wellbore to a depth in the wellbore.

13. The method of claim 9 further comprising determining from the density of the return fluid pore pressure of formation surrounding the wellbore at a selected wellbore depth.

14. The method of claim 9 further comprising determining, using the processor, a pressure gradient of the wellbore during drilling of the wellbore.

15. The method of claim 9 further comprising determining from the density of the return fluid a desired density of the drilling fluid to be supplied to the drill string to maintain a desired pressure gradient in the wellbore.

16. The method of claim 9 further comprising, using the processor, determining effectiveness of hole cleaning during drilling of the wellbore from the determined density of the return fluid.

17. The method of claim 9, further comprising determining a shale density value from a lithology of cuttings over wellbore depth and a determined density and flow rate of the return fluid and determining an overburden gradient from the shale density.

18. The method of claim 17, further comprising determining at least one of pore pressure and fracture pressure from the overburden gradient.

* * * * *